United States Patent [19]

Kauffmann

[11] Patent Number: 5,674,504
[45] Date of Patent: Oct. 7, 1997

[54] COSMETIC COMPOSITION IN THE FORM OF AN AQUEOUS GEL CONTAINING IN SUSPENSION SPHEROIDS OF A NON-HYDROPHILIC, LIPOIDAL SUBSTANCE

[75] Inventor: Myriam Kauffmann, Lyon, France

[73] Assignee: L'Oreal, Paris, France

[21] Appl. No.: 880,422

[22] Filed: May 8, 1992

Related U.S. Application Data

[63] Continuation-in-part of Ser. No. 550,838, Jul. 11, 1990, abandoned.

[30] Foreign Application Priority Data

Jul. 12, 1989 [FR] France ................... 89 09421

[51] Int. Cl.$^6$ ........................................ A61K 7/00
[52] U.S. Cl. ................ 424/401; 424/65; 514/937; 514/938; 514/844; 514/944
[58] Field of Search .................. 424/401, 65, 69, 424/195.1; 514/944, 943, 937, 938, 844

[56] References Cited

U.S. PATENT DOCUMENTS

| | | | |
|---|---|---|---|
| 3,445,563 | 5/1969 | Clegg | 424/35 |
| 4,661,343 | 4/1987 | Zabotto et al. | 424/59 |
| 4,772,471 | 9/1988 | Vanlerberghe et al. | 424/450 |
| 4,880,563 | 11/1989 | Dahms | 252/312 |

FOREIGN PATENT DOCUMENTS

| | | |
|---|---|---|
| 1127039 | 7/1982 | Canada. |
| 0006724 | 1/1980 | European Pat. Off.. |
| 2218086 | 9/1974 | France. |
| 2466273 | 4/1981 | France. |
| 2057957 | 5/1971 | Germany. |
| 2725924 | 12/1978 | Germany. |
| 0061830 | 4/1983 | Japan. |
| 543309 | 2/1942 | United Kingdom. |
| 1328641 | 8/1973 | United Kingdom. |
| 2204792 | 11/1988 | United Kingdom. |

OTHER PUBLICATIONS

French Search Report—FR 89 09421, 1989.

*Primary Examiner*—Gollamudi S. Kishore
*Attorney, Agent, or Firm*—Nixon & Vanderhye, P.C.

[57] ABSTRACT

A cosmetic gel contains spheroids of a non-hydrophilic solid lipoidal substance which improve its emollient and lubricant properties. The spheroids are in the continuous aqueous phase of a suspension and are made of a non-hydrophilic solid lipoidal substance which melts on application to the body. The spheroids have a mean particle diameter between 100 and 3,000 μm and have a melting point below 50° C.

10 Claims, No Drawings

COSMETIC COMPOSITION IN THE FORM OF AN AQUEOUS GEL CONTAINING IN SUSPENSION SPHEROIDS OF A NON-HYDROPHILIC, LIPOIDAL SUBSTANCE

This is a CIP of application Ser. No. 07/550,838 filed Jul. 11, 1990, now abandoned.

This invention relates to a cosmetic composition in the form of an aqueous gel containing in suspension small spheroids of a solid, non-hydrophilic, lipoidal substance which melts on application to the body. The spheroids may be charged with at least one liposoluble or lipoinsoluble cosmetic component.

Numerous cosmetic compositions are formulated as gels, notably makeup removers, tonics, slimming products, anti-sun and after-sun compositions, hair-gels, oral hygiene products such as toothpastes as well as some makeup products such as mascaras.

Gel formulations are particularly sought after because of the amount of water they bring into contact with the skin or oral mucosa (something which provides an agreeable sensation of freshness) and furthermore because gels, when compared to other formulations such as emulsions, do not cause the skin or hair to look greasy.

Gels none the less have certain disadvantages such as their dehydrating effect on the skin, something which leads to a degree of discomfort for the user. Furthermore, they are generally poorly tolerated by dry and occasionally even normal skins.

Very little study has thus far been undertaken to remedy these defects to the extent that for certain applications it has often proved more practical to use emulsions particularly of the oil-in-water type instead of gels. However such emulsions lack freshness and confer on the skin an unwanted greasy and shiny aspect.

Furthermore, the emulsifiers they contain can irritate certain skins, particularly sensitive ones.

In addition, there are some cosmetic components which, when present in large quantities, destabilize the gels or emulsions which contain them. This is particularly so for perfumes and essential oils.

Moreover, the coexistence of two incompatible or interactive components whether in a gel, in an oil dispersed in a gel, or in a classic oil-in-water emulsion, is not possible when the components are in the same phase, nor even when one component is in the external phase and the other in the oily internal phase.

In this last case, the constituents of the oily particles are mobile and thus come into contact with the constituents of the external phase at the level of the interface.

This becomes important for example in certain cosmetic components which, to conserve their properties or to remain stable, must not come into contact with water. Thus, even if such components are incorporated into oil droplets within a gel or emulsion, their mobility assures they remain accessible to water into which they can diffuse or dissolve or in which they can be hydrolysed all of which are undesirable.

After various studies, it has now been found that the disadvantages of gels, notably the drying effect and the consequent lack of comfort, can be resolved by incorporating therein, in the form of a suspension, spheroidal particles of a lipoidal substance, the particles being solid at ambient temperature but able to melt at the raised temperature encountered on application to the body. This endows the gels, with new, particularly emolient and lubricant, properties.

The spheroids of lipoidal substance in effect allow the problem of skin drying to be overcome while bringing to the skin a highly agreeable sensation of comfort.

Moreover, biphasic gel preparations of the oil-in-water type using the spheroids according to the invention are stable without surfactant and the particles of the internal phase are solid. This resolves certain of the problems mentioned above involving the stability of cosmetic components, their conservation and their mutual comparability.

The present invention therefore provides a cosmetic composition in the form of an aqueous gel containing, in suspension in the continuous phase, spheroids of a solid, non-hydrophilic, lipoidal substance which melts on application to the body, the spheroids having a mean particle diameter of from 50 to 10,000 μm and having a melting point of less than 50° C.

The word "body" as used in this specification is intended to mean not only the skin but also the scalp, the hair, nails, teeth and also the buccal mucosa.

According to the invention, the continuous phase of the gel may be water or a mixture of water with a hydroxylated organic solvent such as for example ethanol, glycerin, glycols such as propyleneglycol or glycol ethers such as the monoethylether of diethyleneglycol. In this latter embodiment, the aqueous mixture contains at least 50% of water.

The expression "spheroids" as used in this specification is intended to mean small, solid, essentially spherical or spheroidal particles.

The mean diameter of the spheroids may vary within a very large range, but is preferably between 100 and 3000 μm.

The percentage by weight of spheroids in the gel is of course dependent on the required effect, a higher percentage conferring more pronounced softening and lubricating characteristics on the gel.

In practice, the percentage by weight of spheroids in the gel is generally between 0.1 and 50% by weight, but preferably between 1.5 and 10% by weight.

It is particularly important according to the invention that the melting point of the spheroids be less than 50° C. and preferably between 30° and 45° C. such that they will melt on simple application to the body, or alternatively following light rubbing or massage.

Particularly preferred non-hydrophilic, solid, lipoidal substances for preparing the spheroids include: hemisynthetic glycerides, certain natural fatty substances and certain synthetic fatty compounds.

The possible hemisynthetic glycerides include triglycerides of linear saturated fatty acids having from 8 to 18 carbon atoms and a hydroxyl index of less than 30 and an iodine index of less than 3. Among these are those sold under the denomination "LIPOCIRE A" or "SUPPOCIRE" by GATTEFOSSE, and in particular the following: "SUPPOCIRE AIM"; "AM"; "BM"; "CM"; "DM"; "AI"; "A"; "B"; "C"; and "D" or those sold by Huls Corporation under the names WITEPSOL or SOFTISAN, and in particular the following: "WITEPSOL $H_{32}$"; "$H_{35}$"; "$H_{37}$"; "$H_{39}$"; and "$H_{42}$".

The natural substances which may be used include butters or solid fractions of vegetable fatty bodies such as for example karite butter, cocoa butter, coprah oil and its derivatives.

The synthetic compounds may include silicone waxes such as the products sold under the name "Cire Silicone VP 1622" or "Silicone copolymer F755" by Wacker.

The lipoidal substances enumerated above may be used alone or in the form of a mixture in which case it is preferable to speak in terms of a melting point range or zone, rather than a specific melting point.

It is also possible according to the invention to use lipoidal substances having a melting point above 50° C. but, in this case, it is necessary to have recourse to the additional presence of a lipoidal adjuvant having a lower melting point zone in order to adjust the overall melting point of the mixture.

Among the lipoidal substances having a melting point above 50° C. usable in the form of a mixture with other lipids of lower melting point, one may use triglycerides such as SOFTISAN 154 sold by Dynamit Nobel, animal, vegetable, mineral or synthetic waxes or their derivatives and in particular beeswax, whale blubber, candelilla wax, carnauba wax, their derivatives (particularly following hydrogenation), paraffins, ozokerites, and the product commercialised under the name "ELFACOS $C_{26}$" by Akzo Chemie.

Adjuvants for reducing the melting point of fatty bodies normally melting above 50° C. include linear $C_{14}$ to $C_{16}$ or branched $C_{12}$ to $C_{24}$ saturated fatty alcohols, fatty esters, unsaturated fatty acids, complex lipid mixtures such as vegetable oils, silicone oils etc.

It is also possible to adjust the consistency or the viscosity of the spheroids by introducing into the mixture modified clays (optionally in an oily dispersion), silicas, metallic soaps or any other structural component.

According to a particularly preferred embodiment of the invention, the lipoidal spheroids contain liquid or solid cosmetic components dissolved or dispersed in their structure.

In this embodiment, the lipoidal substance of the spheroids serves as a support and as a vehicle for such components as perfumes, essential oils (or their constituents), pigments, fillers, colourings, vitamins, enzymes and a variety of other cosmetically useful or active substances. Such components may be present in an amount of from 0.01 to 70% and preferably from 1 to 40% referred to the weight of the spheroids.

It goes without saying that when the above mentioned cosmetic components are incorporated or charged into the lipoidal spheroids, it is appropriate to select a lipoidal substance such that after granulation the spheroids maintain their solid form with a melting point zone below 50° C.

The incorporation of perfumes and essential oils in the spheroids is particularly advantageous because it is well known that these elements normally can destabilize gels.

The incorporation of perfumes into the spheroids furthermore permits their protection from oxidation phenomena to which they are particularly sensitive.

This embodiment of the gels according to the invention, ie. the incorporation of spheroids charged with perfume, essential oils (or their constituents), allows the formulation of products rich in these compounds while having an aqueous external phase, something which has not been possible until now.

Possible liposoluble cosmetic components which may be incorporated into the spheroids include more or less liposoluble vitamins or pro-vitamins such as vitamin A and E and their esters, the esters of vitamin C, carotenoids, antiseptics, antiacne agents, or antidandruff agents, UV filters, keratolytic agents such as salicylic acid or its derivatives or salts, molecules acting on natural pigmentation, molecules combatting inflammation such as esters of fatty acid, zinc or copper, emolient fatty esters, mineral, animal, vegetable or synthetic oils, substitutes or components of sebum such as squalene, squalane, ceramides, cholesterol, biological extracts or hair colourings etc . . .

It is also possible to incorporate into the lipoidal spheroids in the form of dispersed solids, cosmetic components which are normally insoluble in such media such as for example hydrosoluble vitamins like vitamin C, biological molecules such as enzymes and any other substance used in cosmetics and which is sensitive to hydrolysis and/or oxidation in aqueous media or to UV radiation.

In the case of substances sensitive to hydrolysis, preferred excipients are those triglycerides having a hydroxyl index lower than 5.

For substances sensitive to oxidation, triglyceride excipients having an iodine index lower than 2 are preferred.

It is also possible to incorporate into the spheroids certain softeners or lubricants for the skin such as talc, the product sold under the name "ORGASOL" by ATO, or in contrast particles intended to produce a rubbing or abrasive effect on the skin or teeth such as powders of polyethylene or other plastic material, vegetable, cellusosic or lignic debris or mineral particles such as silica powders.

According to a variant of this embodiment of the invention, it is possible to prepare gels containing a suspension of spheroids charged with different cosmetic components, something which is of particular interest in the case of mutually incompatible cosmetic components such as perfumes or unsaturated oils and metals or metal oxides.

The spheroids of the gels according to the invention may also contain a small percentage of other components conventionally found in cosmetic lipoidal phases such as antioxidants and preservatives.

Finally, the spheroids may themselves contain other spheres, capsules or molecular vector systems having dimensions as small as a few hundred microns or any other microcapsular or microparticular system. The overall structure is thus one of a compartmentalized spheroid, each compartment being immobilized.

The spheroids of the gels according to the invention may be prepared by any conventional hot or cold granulation or sphere-forming method.

Examples include solidification in the cold of droplets of molten lipoidal substance, maintained under agitation in a non-solvant liquid such as water or by using a cold gas to cool droplets of lipoidal substance sprayed therein or projected therein from a rotating disk, or formed by extrusion or by granulation at raised temperature about a solid nucleus in a turbine or by an air-driven fluidized bed or in a planetary mixer, by passage through a grating or a vibrating grid, by milling, hot or pressurized flow- or injection-moulding, or by cutting or division of a solid lipoidal mass.

Cold preparation methods or those requiring only slight heating, are generally preferred when the cosmetic components included in the lipoidal substance are temperature or oxidation sensitive.

The cooling of the molten droplets is preferably carried out using a gas rather than water when the cosmetic substances contained in the droplets are water sensitive.

Depending on the process chosen and on its parameters, the spheroids obtained, can be finely calibered or be of a greater or lesser size diameter distribution.

The gels according to the invention are obtained according to conventional methods using a gelling agent, generally present in a concentration of from 0.02 to 70% by weight referred to the total weight of the gel (this including the charged or uncharged spheroids).

Particularly suitable gelling agents for the formation of the gels according to the invention include carboxyvinyl polymers such as CARBOPOL 940, neutralized with a mineral or organic base (soda or triethanolamine), polysaccharide gelling agents such as the alginates, xanthane gums, cellulose derivatives, gelatin and mineral gelling agents such as bentones or modified silicas.

The gels according to the invention may also contain in the continuous aqueous phase various hydrosoluble cosmetically acceptable adjuvants and in particular colouring agents, hydrating agents, biological extracts, vitamins or amino acids, or even cosmetically acceptable non-hydrosoluble adjuvants such as fillers or pigments.

The gels according to the invention may also contain, in the continuous aqueous phase, vector systems such as liposomes or nanocapsules or any other system, particularly microcapsular, matricular or micromatricular.

There follow, for the purposes of non-limitative illustration, several examples of preparing charged or uncharged spheroids as well as examples of the gels according to the invention.

General Process for Preparing the Spheroids

The lipoidal substance(s)/active ingredient(s) mixture is prepared at raised temperature.

The solid components of the lipoidal substance are fused at a temperature from 2° to 3° C. higher than that of the lipoidal substance having the highest melting point. Thereafter the other components are added beginning with the least fragile.

The mixture is kept at a temperature 2° to 3° C. above that of its solidification (melting point) zone.

The fragile or volatile components are added last. Any additional solid components are added at the end in the fused mixture and are maintained under agitation.

They may optionally be "fattened" by a fraction of the molten lipoidal substance before their incorporation into the rest of the mixture.

When the mixture is homogeneous, the molten mass is slowly poured into water brought to the same temperature.

The whole is kept under agitation by a rotary system for a few minutes. The molten lipoidal mass then disperses in droplets.

The rotation speed of the system determines the size of the spheroids obtained: particle diameter decreases with increasing speed of rotation.

The dispersion thus obtained is rapidly cooled by addition of water to a temperature of about 0° C. or by immersion into a bath of iced water to a temperature below 0° C. The agitation is stopped when the droplets have solidified. The optionally charged spheroids are then separated by filtration then dried at ambient temperature.

Using the above procedure, uncharged spheroids or spheroids charged with various substances were prepared according to the following examples:

1. Examples of uncharged spheroids
A. mixture of $C_8$-$C_{18}$ hemisynthetic triglycerides  100 g
   (sold under the name "LIPOCIRE A" by Gattefosse)
   fusion zone: 36–38° C.
   average particle size: 1 mm
B. semi-synthetic triglycerides sold under the name  90 g
   "SUPPOCIRE CM" by Gattefosse
   vaseline oil  10 g
   fusion zone: 36–38° C.
   average particle size: 1.5 mm
2. Examples of spheroids charged with perfume
A. perfume concentrate  30 g
   "SUPPOCIRE AI" by Gattefosse  29.748 g
   "SUPPOCIRE DM" by Gattefosse  40 g
   D & C Red 17  0.001 g
   D & C Violet 2  0.001 g
   preservative  0.2 g
   butylhydroxytoluene  0.05 g
   fusion zone: 32–39° C.
   average particle size: 1 mm
B. perfume concentrate  20 g
   "SUPPOCIRE D" by Gattefosse  63.75 g
   myristic alcohol  10 g
   Miglyol gel by Dynamit Nobel  4 g
   nacre  2 g
   butylhydroxytoluene  0.05 g
   preservative  0.2 g
   fusion zone: 33–42° C.
   average particle size: 2 mm
C. perfume concentrate  30 g
   myristic alcohol  10 g
   "SUPPOCIRE B" by Gattefosse  50 g
   "SOFTISAN 154" by Huls Corporation  9.948 g
   D & C Red 17  0.002 g
   butylhydroxytoluene  0.05 g
   fusion zone: 35–42° C.
   average particle size: 500 μm
3. Example of spheroids charged with abrasive powder
   "SUPPOCIRE DM" by Gattefosse  85 g
   perfume concentrate  5 g
   silica powder  10 g
   fusion zone: 39–42° C.
   average particle size: 2 mm
4. Example of spheroids charged with pro-vitamins
   "SUPPOCIRE DM" by Gattefosse  55 g
   myristic alcohol  10 g
   Miglyol gel by Dynamit Nobel  9 g
   α-tocopherol acetate  5 g
   α-tocopherol nicotinate  5 g
   oily carrot extract  15 g
   perfume  1 g
   fusion zone: 34–41° C.
   average particle size: 1 mm
5. Examples of spheroids charged with pigments
A. "SUPPOCIRE B" by Gattefosse  83.20 g
   brown iron oxide  1.55 g
   ocre iron oxide  1.55 g
   titanium dioxide  13.50 g
   preservative  0.20 g
   fusion zone: 39–40° C.
   average particle size: 500 μm
B. "SUPPOCIRE AI" by Gattefosse  73.8 g
   titanium dioxide  20.0 g
   chromium oxide  1.0 g
   talc  5.0 g
   presenative  0.2 g
   fusion zone: 37–39° C.
   average particle size: 200 μm
6. Example of spheroids charged with anti-dandruff agent
   silicone wax SLM 50553/1 by Wacker  99 g
   zinc pyrithione  1 g
   fusion zone: 35–40° C.
   average particle size: 0.2 mm
7. Example of spheroids charged with menthol
   "SUPPOCIRE A" by Gattefosse  79.5 g
   menthol (pharmaceutical grade)  20 g
   chromium oxide  0.5 g
   fusion zone: 25–40° C.
   average particle size: 2.5 mm

EXAMPLES OF GELS

8. Perfumed gels
A. "CARBOPOL 940" by Goodrich  0.3 g
   sodium hydroxide q.s. pH 6.5
   soluble collagen  0.05 g
   glycerin  4 g
   UV filter  0.2 g
   FD & C Blue 1  0.004 g
   preservative  0.02 g
   spheroids charged with perfume according to example 2A  8 g
   water q.s.p.  100 g The clear bluish gel obtained contains heavily perfumed grey spheroids in suspension. On application to the skin, these spheroids melt very quickly releasing the perfume. The aqueous gel of the external phase provides comfort and freshness and the lipoidal substance of the spheroids has a soothing and emollient effect. In addition an adherant, perfumed film remains on the skin.

| | |
|---|---:|
| B. xanthane gum | 1.5 g |
| sorbitol solution up to 70% | 5 g |
| preservative | 0.02 g |
| spheroids charged with perfume according to example 2B | 6 g |
| water q.s.p. | 100 g |
| C. magnesium silicate | 4.5 g |
| glycerin | 6 g |
| propyleneglycol | 2 g |
| preservative | 0.01 g |
| spheroids charged with perfume according to example 2C | 7 g |
| water q.s.p. | 100 g |
| 9. Cleansing gel | |
| "CARBOPOL 940" BY Goodrich | 0.3 g |
| sodium hydroxide q.s. pH = 7 | |
| glycerin | 8 g |
| surfactant ("MIRANOL C2M" by MIRANOL) | 0.3 g |
| preservative | 0.02 g |
| spheroids charged with abrasive powder according to example 3 | 8 g |
| water q.s.p. | 100 g |
| 10. Care gel | |
| "CARBOPOL 1342" by Goodrich | 0.3 g |
| triethanolamine q.s. pH = 6.5 | |
| glycerin | 5 g |
| preservative | 0.01 g |
| spheroids charged with pro-vitamins according to example 4 | 5 g |
| water q.s.p | 100 g |
| 11. Soothing gel | |
| "CARBOPOL 940" by Goodrich | 0.25 g |
| triethanolamine q.s. pH = 6.5 | |
| glycerin | 4 g |
| panthenol | 3 g |
| uncharged spheroids according to example 1B | 6 g |
| water q.s.p. | 100 g |
| 12. Mascara gel | |
| "CARBOPOL 910" by Goodrich | 0.8 g |
| triethanolamine q.s. pH = 6.5 | |
| glycerin | 6 g |
| panthenol | 4 g |
| spheroids charged with pigments according to example 5A | 3 g |
| spheroids charged with pigments according to example 5B | 1 g |
| water q.s.p. | 100 g |

This mascara is introduced into a preferably transparent vessel equipped with a pinching mechanism so that, in use, the brush, initially immersed in the gel within the vessel, on withdrawal is forced to pass through a narrow collar of diameter smaller than that of the brush. This causes disintegration of the microspheres in the gel and leads thus to a dispersion of pigment throughout the aqueous gel on the brush. This allows application of a standard amount of mascara onto the eyelids.

| | |
|---|---:|
| 13. Anti-dandruff gel for the scalp | |
| "CARBOPOL 940" by Goodrich | 0.2 g |
| soda q.s.p. pH = 6.5 | |
| preservative q.s. spheroids charged with zinc pyrithione according to example 6 | 10 g |
| water q.s.p. | 100 g |
| 14. Gingival gel | |
| "LAPONITE XLG" by Laporte Industries Ltd. | 0.23 g |
| sodium carboxymethylcellulose | 0.38 g |
| glycerin | 25 g |
| preservative q.s sodium saccharinate | 0.1 g |
| propyleneglycol extract of rhubarb | 10 g |
| spheroids charged with menthol according to example 7 | 5 g |
| water q.s.p. | 100 g |

The following is a glossary of the trade named materials appearing in the specification.

LIPOCIRE A, by Gattefosse Corporation, 189 Kinder Kamack Road, West Wood, N.J., U.S.A., is a eutectic mixture of fatty acid esters of palm and copra oil, having a melting point (U tube) of 35°–36.5°, a Gardner coloration of 3, an iodide index of 2, a saponification index of 232–242, a hydroxyl index of 20–30 and a peroxide index of 1.

SUPPOCIRE, by Gattefosse Corporation, 189 Kinder Karmack Road, West Wood, N.J. U.S.A., is a trade name for products from natural triglycerides, predominantly lauric, coming from highly selective palm seeds, purified and hydrogenated to remove unsaturated fatty acid generators of undesirable peroxides or from fatty acids proceeding from these same triglycerides by fractionation and distillation. These fatty acids are then esterified in suitable amounts. SUPPOCIRE AIM" has an acid index—<0.2; a saponification index—225/245; a hydroxyl index—<6; an iodide index—<2 and percent unsaponifiables—≦0.5%; SUPPOCIRE AM has an acid index—<0.2; a saponification index—225/245; a hydroxyl index—<6; an iodide index—<2; and percent unsaponifiables—≦0.5%; SUPPOCIRE BM has an acid index—<0.2; a saponification index—225/245; a hydroxyl index—<6; an iodide index—<2; and percent unsaponifiables—<0.5%; SUPPOCIRE CM has an acid index—<0.2; a saponification index—225/245; a hydroxyl index—<6; an iodide index—<2; and percent unsaponifiables—<0.5%; SUPPOCIRE DM has an acid index—<0.2; a saponification index—215/235, a hydroxyl index—<6; an iodide index—<2; and percent unsaponifiables—<0.5%; SUPPOCIRE AI has an acid index—<0.5; a saponification index—225/245; a hydroxyl index—20–30; an iodide index—<2 and percent unsaponifiables—≦0.5%; SUPPOCIRE A has an acid index—<0.5; a saponification index—225/245; a hydroxyl index—20–30; an iodide index—<2 and percent unsaponifiables—<0.5%; SUPPOCIRE C has an acid index—<0.5; a saponification index—220/240; a hydroxyl index—20–30; an iodide index—<2; and percent unsaponifiables—<0.5%; SUPPOCIRE D has an acid index <0.5; a saponification index—215/235; a hydroxyl index—20 –30; an iodide index—<2 and percent unsaponifiables—<0.5%;

WITEPSOL, by Huls Corporation, 80 Centennial Avenue, P.O. Box 365, Piscataway, N.J., U.S.A., are glycerides of fatty acids; WITEPSOL H32 in the glyceride of $C_{10}$–$C_{18}$ fatty acids having an acid index, mgKOH/g—max. 0.2, an iodide index, $gI_2/100$ g—max. 3, a saponification index, mgKOH/g—240-250 and a hydroxyl index, mgKOH/g—max. 3; WITEPSOL H35 is the glyceride of $C_{10}$–$C_{18}$ fatty acids having an acid index, mgKOH/g—max. 0.2, an iodide index, $gI_2/100$ g—max. 3, a saponification index, mgKOH/g—240-250 and a hydroxyl index, mgKOH/g—max. 3; WITEPSOL H37 is the glyceride of $C_{10}$–$C_{18}$ fatty acids having an acid index, mgKOH/g—max. 0.2, an iodide index, $gI_2 100$ g—max. 3, a saponification index, mgKOH/g—225-245, and a hydroxyl index, mgKOH/g—max. 3; WITEPSOL 39.is the glyceride of $C_{10}$–$C_{18}$ fatty acids having an acid index, mgKOH/g—max. 0.2, an iodide index, $gI_2/100$ g—max. 3, a saponification index, mgKOH/g—220-240 and a hydroxyl index, mgKOH/g—max. 3;

WITEPSOL H42 is the glyceride of $C_{10}$–$C_{18}$ fatty acids having an acid index, mgKOH/g—max. 0.2, an iodide index, $gI_2$/100 g—max. 3, a saponification index, mgKOH/g—220–240 and a hydroxyl index, mgKOH/g—max. 3;

SOFTISAN, also by the Huls Corporation, and particularly SOFTISAN 154 is hydrogenated palm oil having an acid value, mgKOH/g—max. 1.0, an iodine value, $gI_2$100 g—max. 3, a saponification value, mgKOH/g—195–210, an unsaponifiable matter, %—max. 0.5, a peroxide value, m e qui $I_2$/kg—max. 2 and a melting point, °C., open capillary method—56–60;

CIRE SILICONE VP 1622 by Wacker-Chemie GmbH, Postfach, D-8000 Munich 22, Fed. Rep. of Germany is a white, crystalline and odorless wax having a melting point (slightly heating 30 g of CIRE SILICONE VP 1622 in a 100 ml beaker)—about 45° C. and a viscosity at 80° C.—max. 15 mm²/s;

SILICONE COPOLYMER F755, also by Wacker-Chemie, above, is stearoxy dimethylpolysiloxane;

ELFACOS $C_{26}$ by Akzo Chemicals Inc., 300 South Riverside Plaza, Chicago, Ill., is a synthetic wax from long chain fatty acids and fatty alcohols, having an acid value—5–10, a saponification value (1.5 hrs)—75–90, a melting point—approx. 80° C., an iodine value—max. 15, a hydroxy value—approx. 120, a pH (5% in IPA/$H_2O$ 1/1)—5–6 and a color Gardner (ASTM D1544-68)—max. 7;

ORGASOL by ATO Chimie and distributed by Lipo Chemical, 202 19th Avenue, Paterson, N.Y., is an ultra fine polyamide powder;

SLM 50553/1 by Wacker Chemie, above, according to CTFA is stearylmethyldimethicone of the chemical type, stearylmethylpolysiloxane;

LAPONITE XLG, by Laporte Absorbents, P.O. Box 2, Moorfield Road, Widnes, Cheshire, U.K., is a synthetic layered silicate with a low heavy metals content. It is insoluble in water but hydrates and swells to give clear and colorless colloidal dispersion in water or aqueous solutions of alcohols. It has the following composition (dry basis): $SiO_2$—59.5%, MgO—27.5%, $Li_2O$—0.8%, $Na_2O$—2.8%, loss on ignition—8.2%, Pb<3 ppm, As<1 ppm, Sb<2 ppm, Cd<2 ppm, Ba<4 ppm and Hg<2 ppm.

We claim:

1. An aqueous gel for cosmetic use containing, in suspension in a continuous aqueous phase, solid spheroids having an average diameter ranging from 100 to 3,000 µm, said solid spheroids comprising a non-hydrophilic lipoidal substance or a non-hydrophilic lipoidal substance having incorporated therein a substance selected from the group consisting of a perfume, an essential oil, a pigment, a filler or an abrasive substance, said solid spheroids having a melting point between 30°–45° C. and melting on application to the body.

2. The aqueous gel of claim 1 wherein said continuous aqueous phase comprises water or a mixture of water with a hydroxylated organic solvent selected from ethanol, glycerine, a glycol or a glycol ether, said mixture containing at least 50 percent water.

3. The aqueous gel of claim 1 wherein said spheroids are present in an amount ranging from 1.5 to 10 percent by weight based on the total weight of said gel.

4. The aqueous gel of claim 1 wherein said non-hydrophilic lipoidal substance is selected from the group consisting of a triglyceride of a $C_8$–$C_{18}$ linear saturated fatty acid, a solid fraction of a vegetable fat and a silicone wax.

5. The aqueous gel of claim 1 wherein said spheroids are charged in an amount ranging from 0.01 to 70 percent by weight based on the total weight of said spheroids.

6. The aqueous gel of claim 1 wherein said spheroids are charged in an amount ranging from 1 to 40 percent by weight based on the total weight of said spheroids.

7. The aqueous gel of claim 1 which also contains a gelling agent present in an amount ranging from 0.02 to 70 percent by weight based on the total weight of said gel.

8. The aqueous gel of claim 1 wherein said continuous aqueous phase also contains at least one hydrosoluble cosmetic adjuvant selected from a coloring agent, a hydrating agent, a biological extract, a vitamin or an amino acid.

9. The aqueous gel of claim 1 wherein said continuous aqueous phase also contains at least one non-hydrosoluble cosmetic adjuvant selected from a filler or a pigment.

10. The aqueous gel of claim 1 wherein said spheroids are present in an amount ranging from 0.1 to 50 percent by weight based on the total weight of said gel.

* * * * *